(12) United States Patent
Murata (10) Patent No.: US 10,379,087 B2
(45) Date of Patent: Aug. 13, 2019

(54) SAMPLE INJECTOR FOR CHROMATOGRAPHY

(71) Applicant: SHIMADZU CORPORATION, Kyoto-shi (JP)

(72) Inventor: Tasuku Murata, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 262 days.

(21) Appl. No.: 15/249,625

(22) Filed: Aug. 29, 2016

(65) Prior Publication Data

US 2018/0059071 A1  Mar. 1, 2018

(51) Int. Cl.
| | |
|---|---|
| *G01N 30/00* | (2006.01) |
| *G01N 30/18* | (2006.01) |
| *G01N 30/12* | (2006.01) |
| *G01N 35/02* | (2006.01) |
| *G01N 30/24* | (2006.01) |
| *G01N 35/04* | (2006.01) |
| *G01N 35/10* | (2006.01) |

(52) U.S. Cl.
CPC ............ *G01N 30/18* (2013.01); *G01N 30/12* (2013.01); *G01N 30/24* (2013.01); *G01N 35/025* (2013.01); *G01N 35/04* (2013.01); *G01N 2035/0441* (2013.01); *G01N 2035/1088* (2013.01)

(58) Field of Classification Search
CPC ...... G01N 30/24; G01N 35/025; G01N 35/04; G01N 2035/0439; G01N 2035/0441; G01N 2035/1088
See application file for complete search history.

(56) References Cited

U.S. PATENT DOCUMENTS

2015/0346069 A1*  12/2015  Inoue ...................... G01N 1/42
73/863.11

FOREIGN PATENT DOCUMENTS

| JP | 50-149087 U1 | 12/1975 | | |
|---|---|---|---|---|
| JP | 9-89860 A | 4/1997 | | |
| JP | 10-104241 A | 4/1998 | | |
| JP | 2005-300277 A | 10/2005 | | |
| JP | 2012177586 A | * | 9/2012 | |
| JP | 2012-177586 A | 9/2013 | | |
| JP | 2015190864 A | * | 11/2015 | ............... G01N 1/42 |
| WO | WO-2014155674 A1 | * | 10/2014 | ............... G01N 1/42 |

OTHER PUBLICATIONS

Communication dated Nov. 29, 2016, from the Japanese Patent Office in counterpart application No. 2014-068500.

* cited by examiner

*Primary Examiner* — Blake A Tankersley
(74) *Attorney, Agent, or Firm* — Sughrue Mion, PLLC (57) ABSTRACT

A sample injector for chromatography 10 where air or moisture can be prevented from getting mixed in when a sample is injected is provided with a syringe 11, a syringe drive unit 13, a turret 12 in which sample vials 4 are placed, a turret drive unit 14, and a control unit 30 that controls the syringe and turret drive units 13 and 14. The configuration includes a housing 15 having a gas introduction port 15a and a gas discharge port 15b that communicate with the inner space, where the syringe 11 sucks a sample from a sample vial 4, the sucked sample is injected into the sample vaporizing chamber 23 in a chromatograph 20, and a predetermined gas is introduced through the gas introduction port 15a, and at the same time, a predetermined gas is discharged through the gas discharge port 15b when a sample is analyzed.

3 Claims, 7 Drawing Sheets

Prior Art

FIG. 6

Prior Art

FIG. 7

Prior Art

SAMPLE INJECTOR FOR CHROMATOGRAPHY

BACKGROUND OF THE INVENTION

1. Field of the Invention

The present invention relates to a sample injector for chromatography having a syringe, and in particular, to a sample injector for gas chromatography with which a great number of liquid samples are analyzed.

2. Description of Related Art

In the case where a liquid sample is analyzed by means of gas chromatography, such an operation is carried out where a certain amount of a liquid sample is sucked from the inside of a sample vial by means of a syringe having a plunger and a barrel with a needle, and after that, the needle is made to penetrate through a septum in the sample vaporizing chamber for gas chromatography so that the liquid sample is injected into the sample vaporizing chamber. Here, the septum is made of silicone or the like having elasticity, and therefore, the hole created when the needle is inserted closes as soon as the needle is removed.

In addition, an automatic sample injector for gas chromatography having a turret where a great number (12, for example) of sample vials into which liquid samples to be analyzed are put, solvent vials into which a solvent for cleaning is put, and waste liquid vials into which a waste liquid is put are aligned is used in order to sequentially and automatically analyze a great number of liquid samples by means of gas chromatography (see Patent Literature 1).

Figure 5:
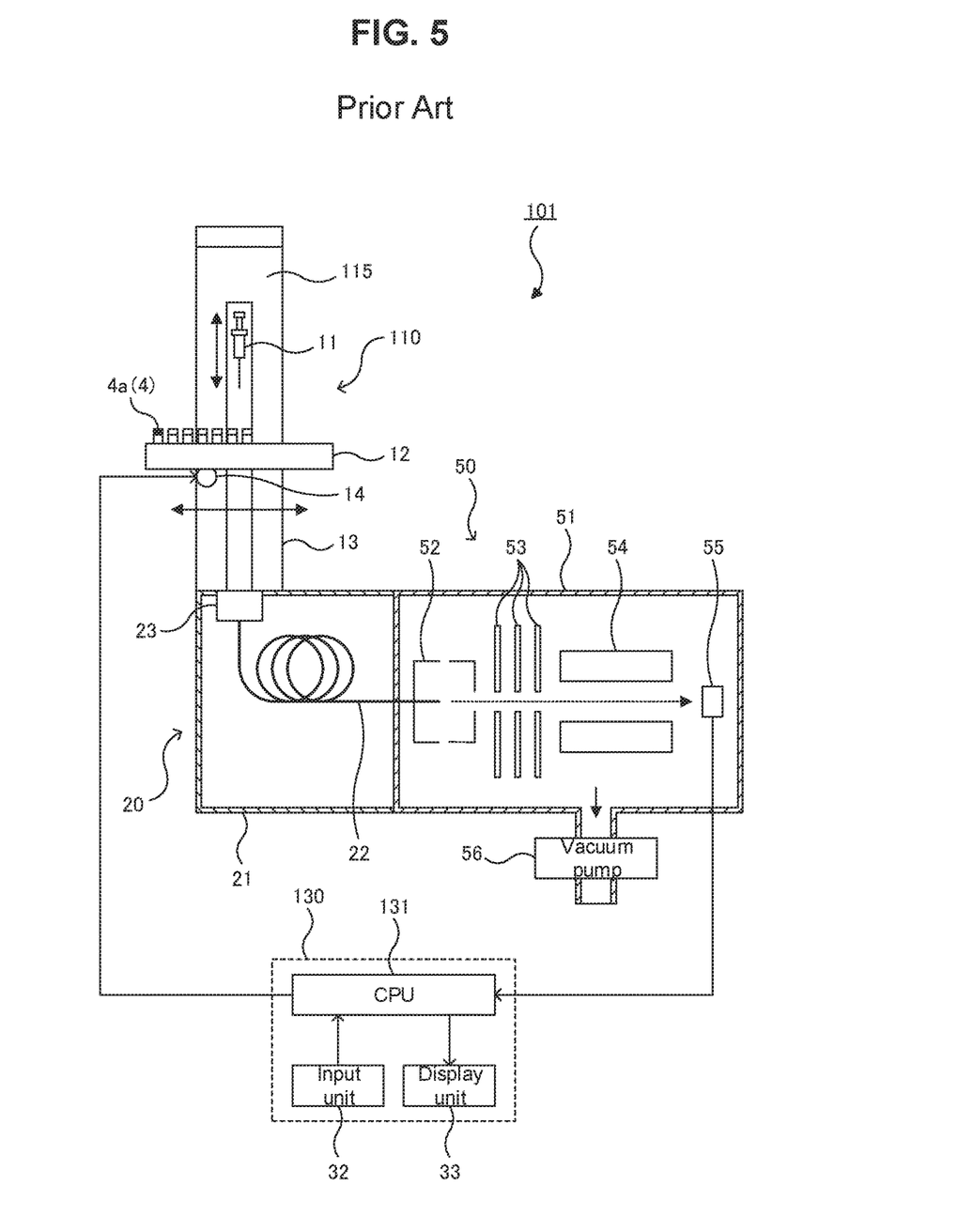
FIG. 5 is a schematic diagram showing the structure of a general GC/MS.
Figure 6:
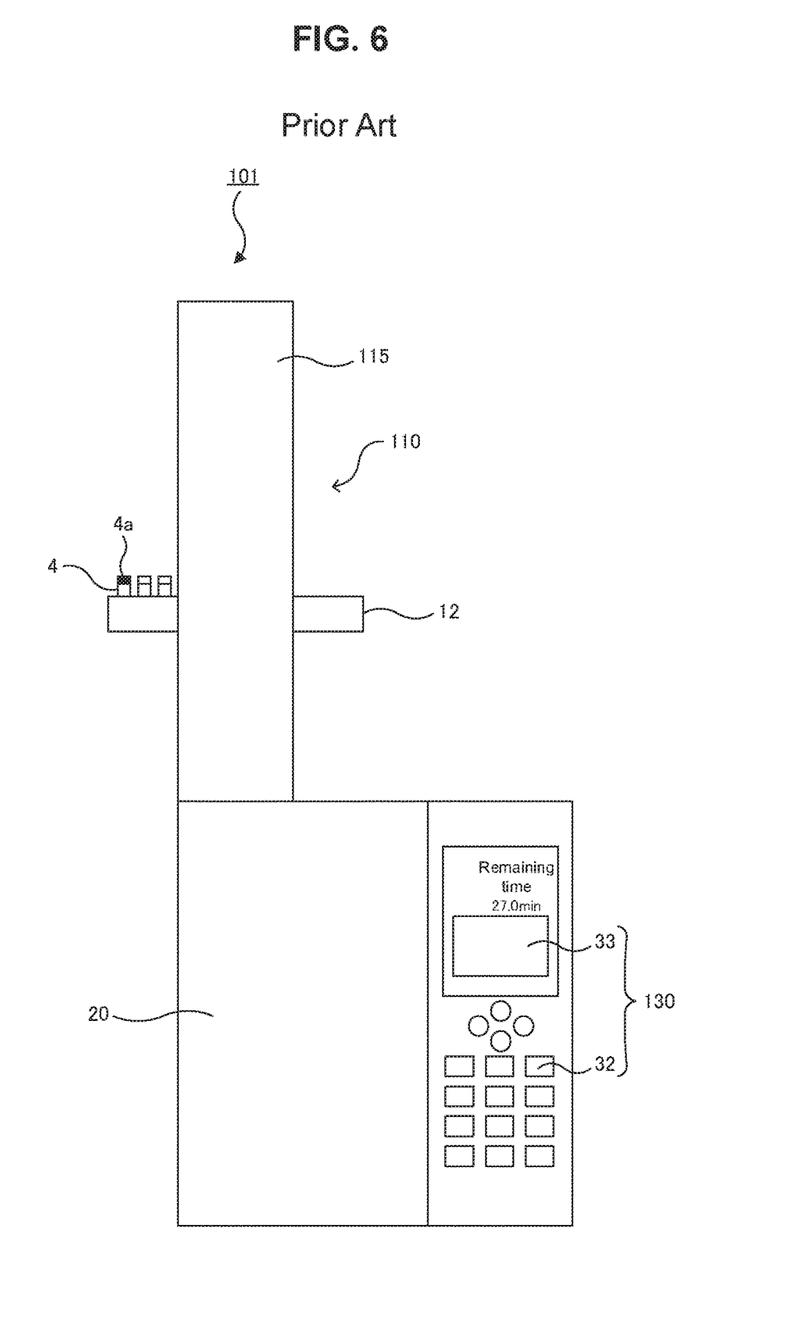
FIG. 6 is a front diagram showing the GC/MS in FIG. 5.
Figure 7:
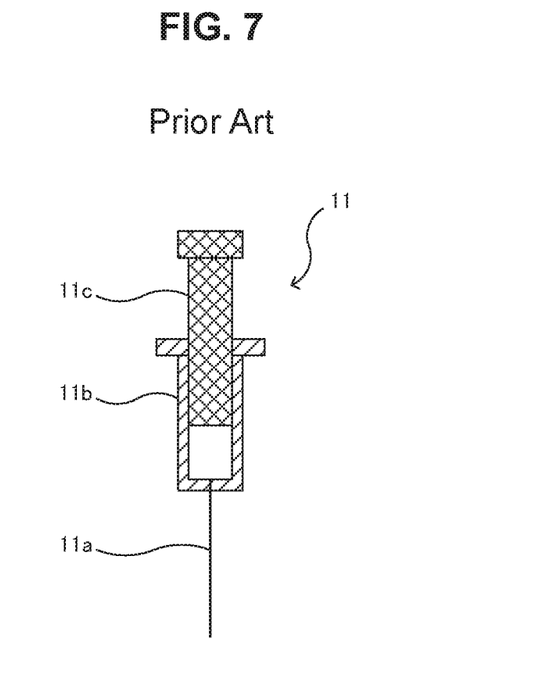
FIG. 7 is a cross-sectional diagram showing the 10 μl syringe in FIG. 5.

FIG. 5 is a schematic diagram showing an example of a gas chromatograph mass spectrometer (GC/MS), and FIG. 6 is a front diagram showing the GC/MS in FIG. 5. In addition, FIG. 7 is a cross-sectional diagram showing the 10 μl syringe 11 in FIG. 5.

A GC/MS 101 is provided with a gas chromatograph 20, an MS unit 50, an automatic sample injector for gas chromatography 110 that is placed in the upper portion of the gas chromatograph 20, and a control unit 130.

The gas chromatograph 20 is provided with an oven 21 for gas chromatography having a housing in cubic form, a column 22 in cylindrical form through which a sample gas passes and that is placed inside the housing 21, and a sample vaporizing chamber 23 that is provided in the upper portion of the housing 21 and is linked to the column 22.

The MS unit 50 is provided with a vacuum chamber 51 in a rectangular parallelepiped form and a vacuum pump 56 for vacuuming the inside of the vacuum chamber 51, and an ionization chamber 52, an ion lens 53, a quadrupole mass filter 54 that works as a mass separator, and a detector 55 for acquiring an ion intensity signal are arranged in this order in the direction in which ions progress.

The control unit 130 is provided with a CPU 131, an input unit 32 and a display unit 33 and controls the gas chromatograph 20, the MS unit 50 and the automatic sample injector for gas chromatography 110.

The automatic sample injector for gas chromatography 110 is provided with a 10 μl syringe 11, a syringe drive unit 13, a turret 12, a turret drive unit 14 and a housing 115 in a rectangular parallelepiped form.

The 10 μl syringe 11 is provided with a barrel 11b having a needle 11a at the end, and a plunger 11c that is fitted and inserted into the barrel 11b so as to be freely slidable.

The syringe drive unit 13 makes it possible for the 10 μl syringe 11 to move in the upward and downward directions relative to the housing 115. Furthermore, it is also possible to push the plunger 11c into the barrel 11b or to pull the plunger 11c out of the barrel 11b.

The thus-formed 10 μl syringe 11 and the syringe drive unit 13 make it possible to suck a liquid sample into the barrel 11b through the needle 11a or to discharge a liquid sample from the inside of the barrel 11b through the needle 11a.

The turret 12 is in a plate form that is long in the lateral direction and on top of which 6 or 12 (n) holes for containing a vial 4 are aligned horizontally. As a result, 6 or 12 vials 4 can be arranged in a line.

Here, the vials 4 are in a cylindrical form with a bottom having a diameter of 10 mm and a height of 24 mm, for example. In addition, a cap 4a made of rubber is attached to the opening at the top of each sample vial 4 into which a liquid sample to be analyzed is put. As a result, a needle 11a is made to penetrate through the cap 4a when a liquid sample within the sample vial 4 is sucked into the 10 μl syringe 11.

In addition, it is necessary to clean the inside of the 10 μl syringe 11 with a solvent for cleaning after one liquid sample has been analyzed and before the next liquid sample is analyzed in order to sequentially and automatically analyze a great number of liquid samples in the gas chromatograph 20. Therefore, solvent vials 4 into which a solvent for cleaning is put and waste liquid vials 4 into which a waste liquid (a solvent for cleaning after use) is put in addition to sample vials 4 are placed in the turret 12. As an example, the user places sample vials 4 in the third to eighth and fourteenth holes in the turret 12, places a solvent for cleaning vial 4 in the first hole, and places a waste liquid vial 4 in the second hole, respectively, before the sequential analysis.

The turret drive unit 14 makes it possible to move the turret 12 in the horizontal direction relative to the housing 115 when a body in disc form rotates.

The thus-formed turret 12 and the turret drive unit 14 make it possible to move the turret 12 in such a manner that a desired vial 4 from among the sample, solvent and waste liquid vials comes beneath the 10 μl syringe 11.

Here, an analysis method for sequentially and automatically analyzing 14 liquid samples in the automatic sample injector for gas chromatography 110 is described.

First, the user uses the input unit 32 to input an instruction "sequential analysis start" so that the control unit 130 controls the sequential and automatic analysis of 14 samples vials 4.

Typically, the control unit 130 first allows the turret drive unit 14 to move the turret 12 so that a sample vial 4 comes beneath the 10 μl syringe 11, and after that allows the syringe drive unit 13 to lower the 10 μl syringe 11 so that the needle 11a is inserted into the sample vial 4. In addition, the control unit 130 allows the syringe drive unit 13 to pull the plunger 11c so that the liquid sample is sucked into the barrel 11b from the sample vial 4, and after that allows the syringe drive unit 13 to raise the 10 μl syringe 11 so that the needle 11a is pulled out of the sample vial 4.

Next, the turret drive unit 14 is allowed to move the turret 12 so that the turret 12 is not placed beneath the 10 μl syringe 11, and after that, the syringe drive unit 13 is allowed to lower the 10 μl syringe 11 so that the needle 11a is inserted into the sample vaporizing chamber 23 through the septum (not shown). In addition, the syringe drive unit 13 is allowed to push the plunger 11c so that the liquid sample is injected into the sample vaporizing chamber 23 from the barrel 11b, and after that, the syringe drive unit 13 is allowed to raise the 10 μl syringe 11 so that the needle 11a is pulled out of the sample vaporing chamber 23 through the septum.

Next, the turret drive unit 14 is allowed to move the turret 12 so that the solvent vial 4 in the fifteenth hole comes beneath the 10 μl syringe 11, and after that, the syringe drive unit 13 is allowed to lower the 10 μl syringe 11 so that the needle 11a is inserted into the solvent vial 4. Then, the syringe drive unit 13 is allowed to pull the plunger 11c so that the solvent for cleaning is sucked into the barrel 11b from the solvent vial 4, and after that, the syringe drive unit 13 is allowed to raise the 10 μl syringe 11 so that the needle 11a is pulled out of the solvent vial 4.

Next, the turret drive unit 14 is allowed to move the turret 12 so that the waste liquid vial 4 in the sixteenth hole comes beneath the 10 μl syringe 11, and after that, the syringe drive unit 13 is allowed to lower the 10 μl syringe 11 so that the needle 11a is inserted into the waste liquid vial 4. Then, the syringe drive unit 13 is allowed to push the plunger 11c so that the solvent for cleaning is discharged into the waste liquid vial 4 from the barrel 11b, and after that, the syringe drive unit 13 is allowed to raise the 10 μl syringe 11 so that the needle 11a is pulled out of the waste liquid vial 4.

In the same manner, the remaining thirteen sample vials 4 are sequentially and automatically analyzed.

CITATION LIST

Patent Literature

Patent Literature 1: Japanese Unexamined Patent Publication H10 (1998)-104241

SUMMARY OF THE INVENTION

1. Problem to be Solved by the Invention

In the above-described automatic sample injector for gas chromatography 110, a microscopic amount of air sometimes gets mixed in through the gap between the needle 11a and the septum when the needle 11a is inserted into the sample vaporizing chamber 23 through the septum. In addition, the moisture in the air that adheres to the end portion of the needle 11a may be detected depending on the type of the detector 55 (a barrier discharge ionization detector, for example) when the 10 μl syringe 11 that has been left in the air is used, and this becomes an obstacle component when air or moisture is included in the components to be analyzed, and thus, a problem arises such that the sample to be analyzed cannot be precisely analyzed.

Therefore, an object of the present invention is to provide a sample injector for chromatography where air or moisture can be prevented from getting mixed in when a sample is injected.

2. Means for Solving Problem

In order to solve the above-described problem, the sample injector for chromatography according to the present invention is provided with: a syringe that comprises a barrel having a needle at an end and a plunger that is fitted and inserted into the barrel so as to be freely slidable; a syringe drive unit that can move the above-described syringe in the upward and downward directions and that can push in or pull out the above-described plunger; a turret in which sample vials into which samples to be analyzed are put are placed; a turret drive unit that can move the above-described turret in a horizontal direction; and a control unit that controls the above-described syringe drive unit and the turret drive unit, wherein a housing having a gas introduction port and a gas discharge port that communicate with the inner space is provided, the above-described syringe is allowed to suck a sample to be analyzed from a sample vial, and it is possible to inject the sucked sample to be analyzed into a sample vaporizing chamber in a chromatograph within the inner space of the above-described housing, and a predetermined gas is introduced through the above-described gas introduction port and a predetermined gas is discharged through the above-described gas discharge port when a sample to be analyzed is analyzed.

Here, the "predetermined gas" is any type of gas that is determined by the user and is a gas that does not include a component to be analyzed, for example.

3. Effects of the Invention

As described above, in the sample injector for chromatography according to the present invention, the "predetermined gas" with which the inner space of the housing can be purged can be selected so that the components that are involved at the time of injection into the sample vaporizing chamber can be selected. In addition, moisture that is absorbed in the end portion of the needle of the syringe can be removed by continuing purging with a gas that does not include moisture over a long period of time. As a result, a more precise assay is possible by preventing an obstacle due to disturbance when a microscopic amount of moisture and air in a sample to be analyzed is analyzed.

Other Means for Solving Problem and Effects Thereof

In addition, the sample injector for chromatography according to the present invention is provided with: a syringe that comprises a barrel having a needle at an end and a plunger that is fitted and inserted into the barrel so as to be freely slidable; a syringe drive unit that can move the above-described syringe in the upward and downward directions and that can push in or pull out the above-described plunger; a turret in which sample vials into which samples to be analyzed are put are placed; a turret drive unit that can move the above-described turret in a horizontal direction; and a control unit that controls the above-described syringe drive unit and the turret drive unit, wherein a gas introduction port that communicates with an inner space and a tube that is expandable and contractible in the upward and downward directions are provided, the above-described tube is attached to the above-described syringe in such a manner that when the end of the above-described needle is placed in the inner space of the tube in an expanded state and the above-described tube contracts, the above-described syringe can suck a sample to be analyzed from a sample vial, and it becomes possible for the sucked sample to be analyzed to be injected into the sample vaporizing chamber of a chromatograph, and a predetermined gas is introduced through the above-described gas introduction port when a sample to be analyzed is analyzed.

Here, "expandable and contractible in the upward and downward directions" means a bellow form, for example.

As described above, in the sample injector for chromatography according to the present invention, the "predetermined gas" with which the inner space of the tube is purged can be selected so that the components that are involved at the time of the injection into the sample vaporizing chamber can be selected. In addition, the tube can be continued to be purged with a gas that does not include moisture over a long period of time so that the moisture that is absorbed in the end portion of the needle of the syringe can be removed. As a result, a more precise assay is possible by preventing an obstacle due to disturbance when a microscopic amount of moisture and air in a sample to be analyzed is analyzed.

In addition, in the sample injector for chromatography according to the present invention, a number of sample vials may be placed in the above-described turret.

Furthermore, in the sample injector for chromatography according to the present invention, the above-described sample vaporizing chamber may be provided with a septum through which the above-described needle is inserted.

DETAILED DESCRIPTION OF EMBODIMENTS

In the following, the embodiments of the present invention are described in reference to the drawings. Here, the present invention is not limited to the below-described embodiments, and naturally include various modifications as long as the gist of the present invention is not deviated from.

First Embodiment

Figure 1:
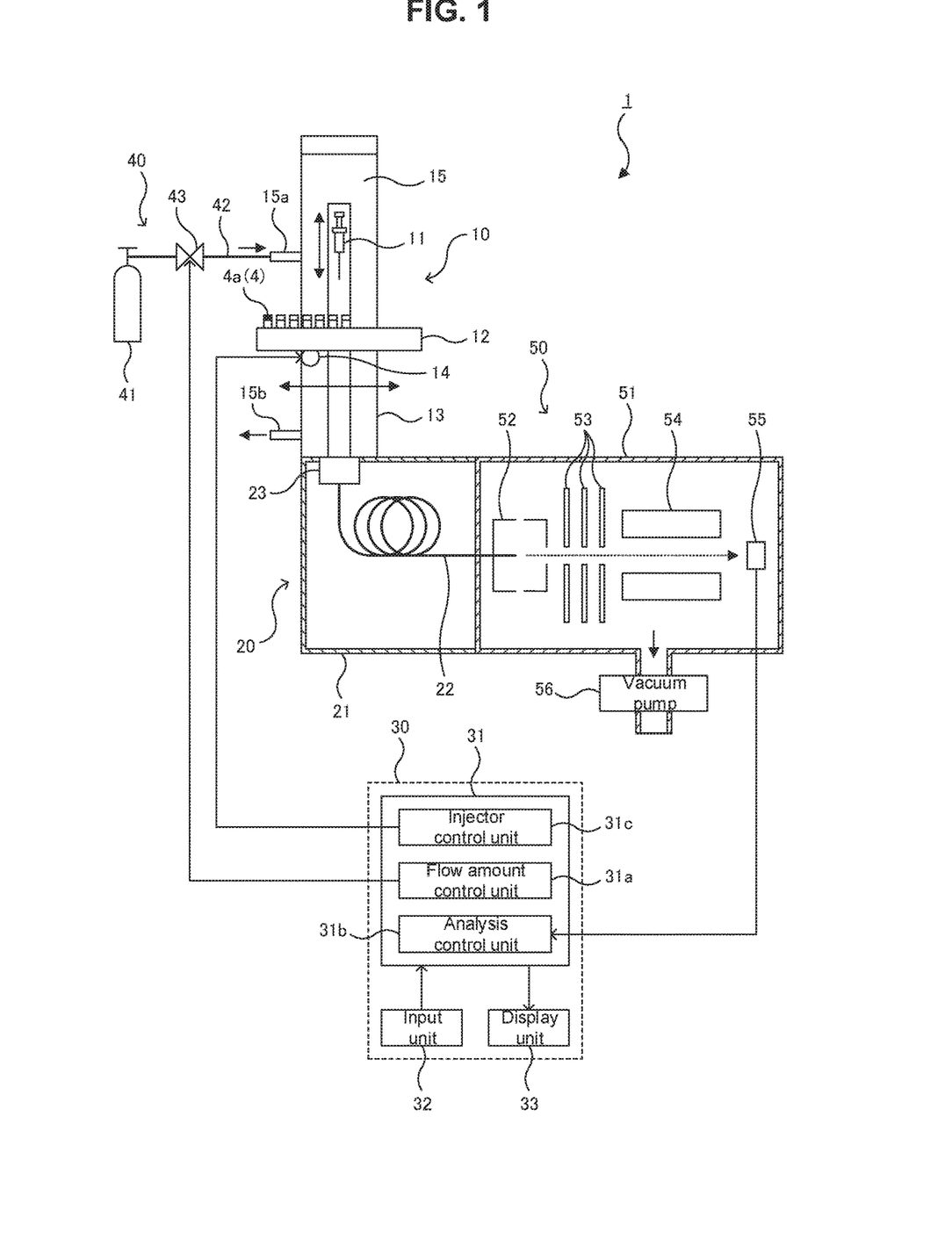
FIG. 1 is a schematic diagram showing the structure of the GC/MS according to the first embodiment.
Figure 2:
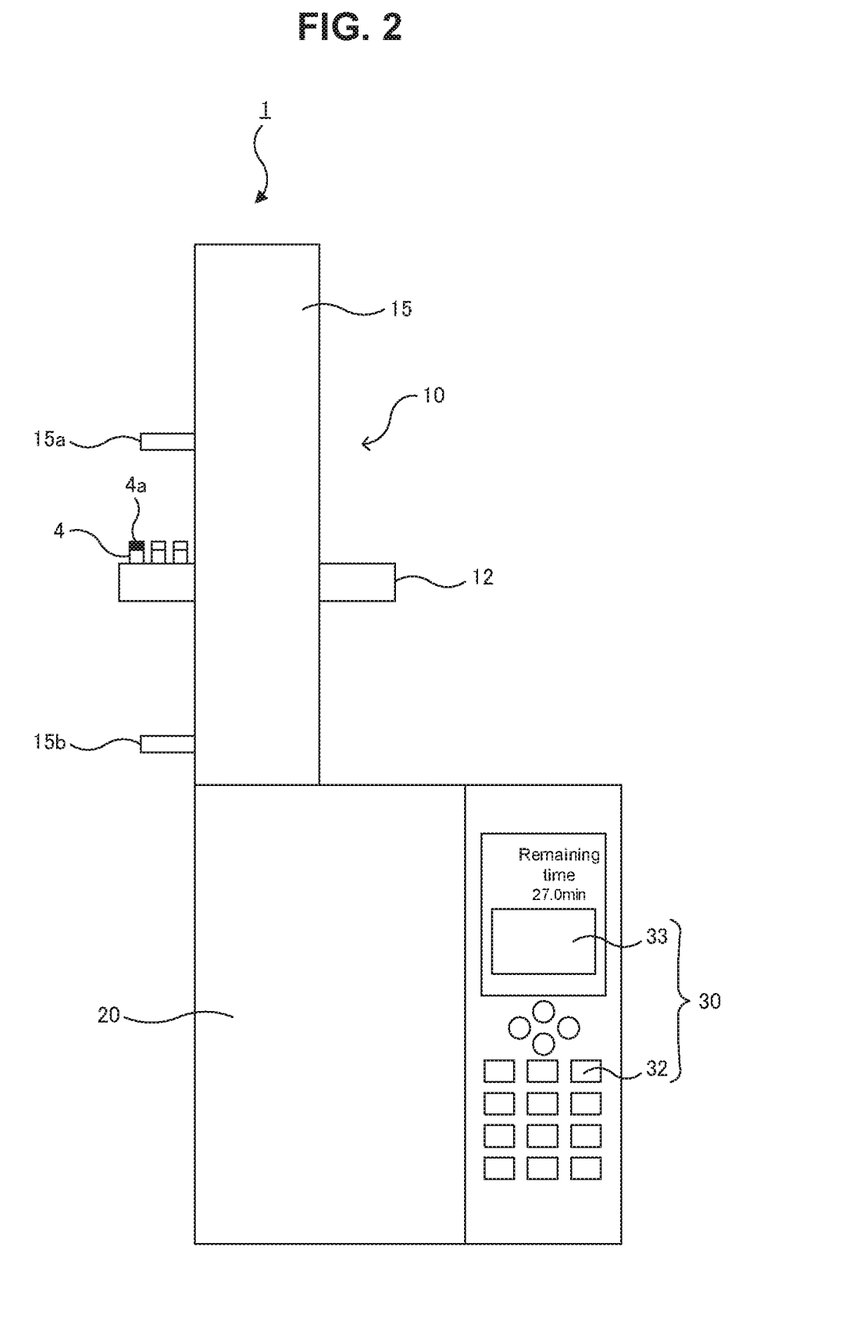
FIG. 2 is a front diagram showing the GC/MS in FIG. 1.

FIG. 1 is a schematic diagram showing the structure of the GC/MS according to the first embodiment of the present invention, and FIG. 2 is a front diagram showing the GC/MS in FIG. 1. Here, the same symbols are attached to the same components as in the above-described conventional GC/MS 101.

A GC/MS 1 is provided with a gas chromatograph 20, an MS unit 50, an automatic sample injector for gas chromatography 10 provided in the upper portion of the gas chromatograph 20, a flow amount control unit 40 and a control unit 30. Here, the control unit 30 may be provided so as to be separated for each function, that is to say, the gas chromatograph 20, the automatic sample injector for gas chromatography 10, the flow amount control unit 40 and the MS unit 50 may respectively be provided with a control unit.

The automatic sample injector for gas chromatography 10 is provided with a 10 μl syringe 11, a syringe drive unit 13, a turret 12, a turret drive unit 14 and a housing 15 in a rectangular parallelepiped form.

A gas introduction port 15a in cylindrical form is created in an upper portion of the housing 15, and at the same time, a gas discharge port 15b in cylindrical form is created in a lower portion of the housing 15. As a result, a gas that has been introduced into the inner space of the housing 15 through the gas introduction port 15a flows towards the bottom through the inner space of the housing 15 so as to be discharged to the outside of the housing 15 through the gas discharge port 15b.

A predetermined gas is sealed in a gas supply source 41. In addition, one end portion of a gas introduction pipe 42 is connected to the gas supply source 41, a gas flow amount adjusting valve 43 is provided in the middle of the gas introduction pipe 42, and the other end portion of the gas introduction pipe 42 is connected to the gas introduction port 15a so that the gas supply source 41, the gas introduction pipe 42 and the gas flow amount adjusting valve 43 form a flow amount control unit 40 for supplying a predetermined gas. Here, a gas supply source 41 in which a gas of any type that is selected by the user is sealed can be attached to one end portion of the gas introduction pipe 42.

The control unit 30 is provided with a CPU 31, an input unit 32 and a display unit 33 and controls the gas chromatograph 20, the MS unit 50, the automatic sample injector for gas chromatography 10 and the flow amount control unit 40.

The functions processed by the CPU 31 can be described as blocks, including a flow amount control unit 31a for controlling the flow amount control unit 40, an analysis control unit 31b for receiving an ion intensity signal from a detector 55, and an injector control unit 31c for controlling the automatic sample injector for gas chromatography 10.

The flow amount control unit 31a controls the gas flow amount adjusting valve 43 so that a predetermined amount of gas flows through the gas introduction pipe 42 from the gas supply source 41. For example, the user uses the input unit 32 so as to input an instruction "sequential analysis start" at the time of analysis so that the gas flow amount adjusting valve 43 can be controlled so as to supply a predetermined gas into the inner space of the housing 15 from the gas supply source 41 through the gas introduction pipe 42 and the gas introduction port 15a.

As described above, in the GC/MS 1 according to the first embodiment, the "predetermined gas" with which the inner space of the housing 15 is purged can be selected so that the components that are involved at the time of injection into the sample vaporizing chamber 23 can be selected. In addition, the inner space can be continued to be purged with a gas that does not include moisture over a long period of time so that moisture that is absorbed in the end portion of the needle 11a of the syringe 11 can be removed. As a result, a more precise assay is possible by preventing an obstacle due to disturbance when a microscopic amount of moisture and air in a sample to be analyzed is analyzed even in the case where a barrier discharge ionization detector is used as the detector 55.

Second Embodiment

Figure 3:
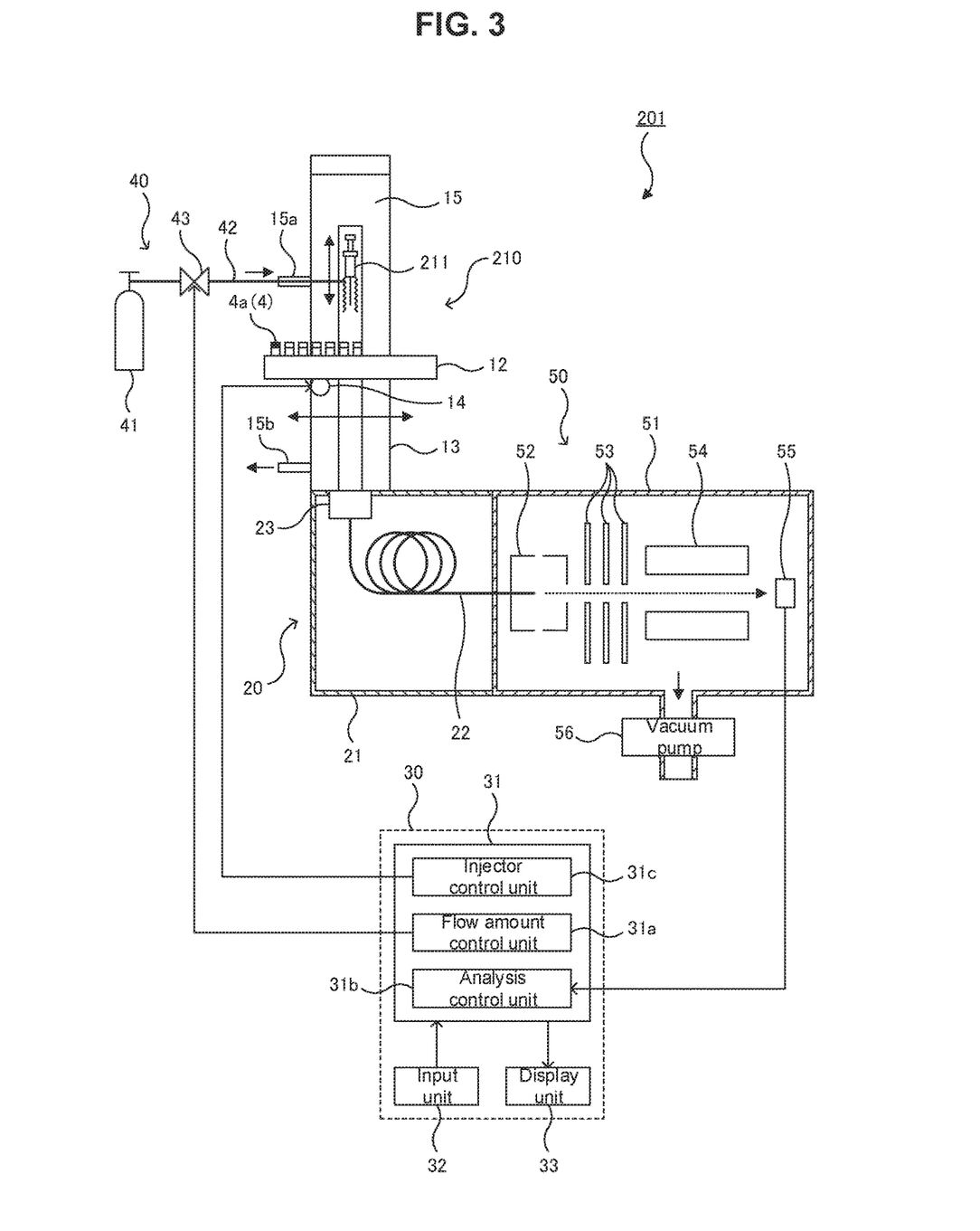
FIG. 3 is a schematic diagram showing the structure of the GC/MS according to the second embodiment.
Figure 4A:
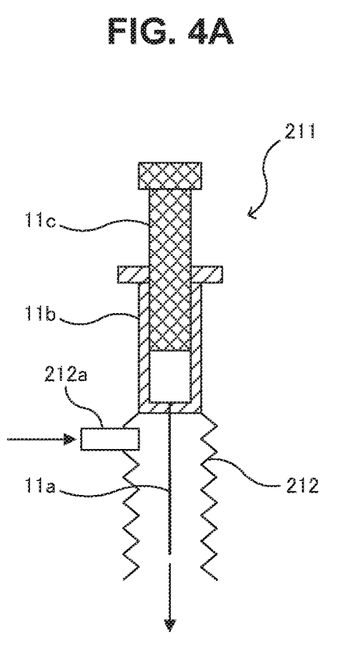
FIGS. 4A and 4B are cross-sectional diagrams showing the 10 μl syringe in FIG. 3.
Figure 4B:
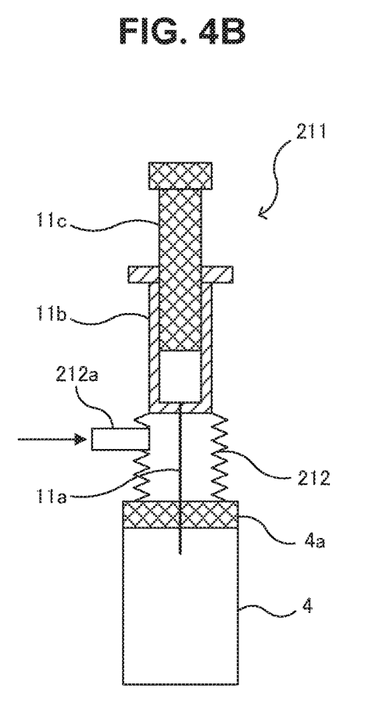

FIG. 3 is a schematic diagram showing the structure of the GC/MS according to the second embodiment of the present invention, and FIGS. 4A and 4B are cross-sectional diagrams showing the 10 μl syringe 211 in FIG. 3. Here, the same symbols are attached to the same components as in the GC/MS 1 and GC/MS 101.

A GC/MS 201 is provided with a gas chromatograph 20, an MS unit 50, an automatic sample injector for gas chromatography 210 provided in the upper portion of the gas chromatograph 20, a flow amount control unit 40 and a control unit 30.

The automatic sample injector for gas chromatography 210 is provided with a 10 μl syringe 211, a syringe drive unit 13, a turret 12, a turret drive unit 14 and a housing 15 in a rectangular parallelepiped form, and a gas introduction port 15a in cylindrical form is created in an upper portion of the housing 15, and at the same time, a gas discharge port 15b in cylindrical form is created in a lower portion of the housing 15.

The 10 μl syringe 211 is provided with a barrel 11b having a needle 11a at an end, a plunger 11 that is fitted and inserted into the barrel 11b so as to be freely slidable, and a tube 212 attached to the outer periphery portion at the end of the barrel 11b.

The tube 212 has an approximately cylindrical body in a bellow form that is expandable and contractible in the upward and downward directions, and a gas introduction port 212a in cylindrical form is created in an upper portion of the tube 212. As a result, a gas that has been introduced into the inner space of the tube 212 through the gas introduction port 212a flows towards the bottom through the inner space of the tube 212 so as to be discharged to the outside of the tube 212 through the opening below.

In the thus-formed 10 μl syringe 211, the tube 212 is in a contracted state when the upper surface of a sample vial 4 and the lower surface of the tube 212 make contact with each other, and a liquid sample can be sucked into the barrel 11b through the needle 11a, or a liquid sample can be discharged from the barrel 11b through the needle 11a (see FIG. 4B). In addition, the tube 212 is in such a state as to be expanded to a predetermined length when the lower surface of the tube 212 does not make contact with anything, and the end of the needle 11a is located inside the tube 212 (see FIG. 4A).

A predetermined gas is sealed in the gas supply source 41. In addition, one end portion of a gas introduction pipe 42 is connected to the gas supply source 41, a gas flow amount adjusting valve 43 is provided in the middle of the gas introduction pipe 42, and the other end portion of the gas introduction pipe 42 is connected to the gas introduction port 212a through the gas introduction port 15a so that the gas supply source 41, the gas introduction pipe 42 and the gas flow amount adjusting valve 43 form a flow amount control unit 40 for supplying a predetermined gas.

As described above, in the GC/MS 201 according to the second embodiment, the "predetermined gas" with which the inner space of the tube 212 is purged can be selected so that the components that are involved at the time of injection into the sample vaporizing chamber 23 can be selected. In addition, the inner space can be continued to be purged with a gas that does not include moisture over a long period of time so that moisture that is absorbed in the end portion of the needle 11a of the syringe 11 can be removed. As a result, a more precise assay is possible by preventing an obstacle due to disturbance when a microscopic amount of moisture and air in a sample to be analyzed is analyzed even in the case where a barrier discharge ionization detector is used as the detector 55.

Other Embodiments

Though the flow amount control unit 31a has such a structure that the gas flow amount adjusting valve 43 can be controlled when the user uses the input unit 32 so as to input an instruction "sequential analysis start" in the above-described GC/MS, an alternative structure may be possible where the user uses the input unit 32 so as to input "open" or "close" according to an appropriate timing in order to control the gas flow amount adjusting valve 43.

INDUSTRIAL APPLICABILITY

The present invention can be applied to a chromatograph mass spectrometer.

EXPLANATION OF SYMBOLS 4 vial
10 sample injector for gas chromatography
11 syringe
11a needle
11b barrel
11c plunger
12 turret
13 syringe drive unit
14 turret drive unit
15 housing
15a gas introduction port
15b gas discharge port
23 sample vaporizing chamber
30 control unit

What is claimed is:

1. A sample injector for chromatography, comprising:

a syringe that comprises a barrel having a needle at an end thereof and a plunger that is fitted and inserted into the barrel so as to be freely slidable therein;

a syringe drive unit configured to move said syringe in upward and downward directions and to push in or pull out said plunger;

a turret into which a sample vial is placed, the sample vial being a vial into which a sample to be analyzed is placed;

a turret drive unit configured to move said turret in a horizontal direction;

a housing having an inner space, a gas introduction port and a gas discharge port, the gas introduction port and the gas discharge port communicating with the inner space, and the gas introduction port being connected to a gas supply source, a flow amount control unit including a gas flow adjusting valve, the flow amount control unit configured to control a flow of a predetermined gas introduced into the inner space by the gas introduction port, and a control unit configured to control the syringe drive unit, the turret drive unit, and the flow amount control unit, wherein said syringe is configured to suck the sample to be analyzed from the sample vial, and inject the sucked sample to be analyzed into a sample vaporizing chamber in a chromatograph from the inner space of said housing, and wherein the flow amount control unit is configured to introduce the predetermined gas from the gas introduction port so as to flow within the inner space and to exit the inner space from the gas discharge port when the sample to be analyzed is analyzed.

2. The sample injector for chromatography according to claim 1, wherein a plurality of sample vials are placed in said turret.

3. The sample injector for chromatography according to claim 1, the sample injector further comprising the sample vaporization chamber, wherein the sample vaporizing chamber including a septum through which said needle is insertable.

* * * * *